United States Patent
Zalkin et al.

(10) Patent No.: US 6,586,216 B2
(45) Date of Patent: Jul. 1, 2003

(54) DEREGULATION OF GLUTAMINE PRPP AMIDOTRANSFERASE ACTIVITY

(75) Inventors: Howard Zalkin, West Lafayette, IN (US); Janet L. Smith, Lafayette, IN (US); Robert L. Switzer, Urbana, IL (US)

(73) Assignees: Purdue Research Foundation, West Lafayette, IA (US); The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/805,294

(22) Filed: Mar. 13, 2001

(65) Prior Publication Data

US 2001/0031486 A1 Oct. 18, 2001

Related U.S. Application Data

(63) Continuation of application No. 09/150,440, filed on Sep. 9, 1998, now Pat. No. 6,204,041
(60) Provisional application No. 60/058,216, filed on Sep. 9, 1997.

(51) Int. Cl.[7] .............................. C12N 9/10; C12N 1/20; C12N 15/00; C12P 19/30; C07H 21/04
(52) U.S. Cl. ...................... 435/193; 435/252.3; 435/89; 435/440; 536/23.2
(58) Field of Search ............................ 435/193, 252.3, 435/89, 440; 536/23.2

(56) References Cited

PUBLICATIONS

Zhou et al. Binding of purine nucleotides to two regulatory sites results in synergistic feedback inhibition of glutamine PRPP amidotransferase. JBC, vol. 269, No. 9, pp. 6784–6789 (1994).*

Muchmore et al. Crystal structure of glutamine PRPP amidotransferase from *Escherichia coli*. Protein Science, vol. 7, pp. 39–51 (1998).*

"Mechanism of the Synergistic End–Product Regulation of *Bacillus subtilis* Glutamine Phosphoribosylpyrophosphate Amidotransferase by Nucleotides", Chen, et al., *Biochemistry*, vol. 36, No. 35, 1997, pp. 10718–10726.

"Glutamine Phosphoribosylpyrophosphate Amidotransferase from *Escherichia coli*", Messenger, et al., *Journal of Biological Chemistry*, vol. 254, No. 9, May 10, 1979, pp. 3382–3392.

"Purification and Properties of Glutamine Phosphoribosylpyrophosphate Amidotransferase from *Bacillus subtilis*", Wong, et al., *Biochemistry*, vol. 20, No. 20, 1981, pp. 5669–5674.

(List continued on next page.)

*Primary Examiner*—Ponnathapu Achutamurthy
*Assistant Examiner*—Yong Pak
(74) *Attorney, Agent, or Firm*—Barnes & Thornburg

(57) ABSTRACT

The present invention is directed to a modified amidotransferase. The amino acid sequence of the modified amidotransferase differs from the amino acid sequence of a native *E. coli* glutamine PRPP amidotransferase in that one or more amino acid residues of the modified amidotransferase are substituted at positions equivalent to amino acid positions in Bacillus amidotransferase selected from the group consisting of 282, 283, 307, and 347 of SEQ ID NO:1, wherein the modified amidotransferase is less sensitive to end-product inhibition than is the native *E. coli* glutamine PRPP amidotransferase.

2 Claims, 1 Drawing Sheet

OTHER PUBLICATIONS

"Structure of the Allosteric Regulatory Enzyme of Purine Biosynthesis", Smith et al., *Science*, vol. 264, Jun. 3, 1994, pp. 1427–1433.

"Regulation of *Bacillus subtilis* Glutamine Phosphoribosylpyrophosphate Amidotransferase Activity by End Products", Meyer et al., *Journal of Biological Chemistry*, vol. 254, No. 12, Jun. 25, 1979, pp. 5397–5402.

"Binding of Purine Nucleotides to Two Regulatory Sites Results in Synergistic Feedback Inhibition of Glutamine 5–Phosphoribosylpyrophosphate Amidotransferase", Zhou et al., *J. Biol. Chem.*, vol. 269, No. 9, Mar. 4, 1994, pp. 6784–6789.

"Rapid and Efficient Site–Specific Mutagenesis without Phenotypic Selection", Kunkel et al., *Methods in Enzymology*, vol. 154, 1987, pp. 367–382.

"Nucleotide Sequence of *Escherichia coli* purF and Deduced Amino Acid Sequence of Glutamine Phosphoribosylpyrophosphate Amidotransferase", Tso et al., *Journal of Biological Chemistry*, vol. 257, No. 7, Apr. 10, 1982, pp. 3525–3531.

"Nucleotide Sequence of the *Escherichia coli* purF Gene Encoding Amidophosphoribosyltransferase for de novo Purine Nucleotide Synthesis", Sampei et al., *Nucleic Acids Research*, vol. 16, No. 17, 1988, p. 8717.

"Cloning of the *Bacillus subtilis* Glutamine Phosphoribosylpyrophosphate Amidotransferase Gene in *Escherichia coli*", Makaroff et al., *Journal of Biological Chemistry*, vol. 258, No. 17, Sep. 10, 1983, pp. 10586–10593.

* cited by examiner

# DEREGULATION OF GLUTAMINE PRPP AMIDOTRANSFERASE ACTIVITY

CROSS REFERENCE TO RELATED APPLICATIONS

This application is a continuation application of U.S. patent application Ser. No. 09/150,440 issed as U.S. Pat. No. 6,204,041, filed Sep. 9, 1998, which claims priority to U.S. Provisional Patent Application Ser. No. 60/058,216, filed Sep. 9, 1997.

FIELD OF THE INVENTION

This invention relates to the deregulation of purine nucleotide biosynthesis. More particularly, this invention is directed to the modification of glutamine phosphoribosylpyrophosphate (PRPP) amidotransferase to decrease end-product inhibition of glutamine PRPP amidotransferase activity.

BACKGROUND

Glutamine PRPP amidotransferase catalyzes the initial reaction in de novo purine nucleotide synthesis and is the key regulatory enzyme in the pathway. Genes encoding glutamine PRPP amidotransferase have been cloned from more than 20 organisms including bacteria, eukarya, and archea. In particular, the enzymes from *Escherichia coli* and *Bacillus subtilis* have been purified to homogeneity and are well-characterized, including having the X-ray structures determined for these enzyme species. The *E. coli* and *B. subtilis* enzymes are both homotetramers and are representative of two classes of glutamine PRPP amidotransferases. Enzymes of the *B. subtilis* class are synthesized with an $NH_2$ terminal propeptide and an Fe—S center, whereas enzymes of the *E. coli* class have neither.

Purine nucleotide biosynthesis is regulated, at both the gene (transcription/translation) and the protein (enzymatic activity) level. Attempts at increasing the biosynthesis of purine nucleotides have focused on the deregulation of genes encoding pathway enzymes. However, the enzymatic activity of a key pathway enzyme, glutamine PRPP amidotransferase, is inhibited by the pathway end-products, adenine and guanine nucleotides. Therefore an effective strategy for enhancing host cell production of purine nucleotides includes the use of a modified glutamine PRPP amidotransferase, wherein the modification reduces the sensitivity of the enzyme to end-product inhibition by adenine and guanine nucleotides.

The two classes of glutamine PRPP amidotransferase enzymes (as represented by the *E. coli* and *B. subtilis* enzymes) exhibit different end-product inhibitory patterns by adenine and guanine nucleotides. GMP is the single strongest inhibitor of *E. coli* glutamine PRPP amidotransferase, and AMP is the strongest inhibitor of the *B. subtilis* enzyme. Notwithstanding this difference, there is one common distinctive characteristic of the inhibition by nucleotides. Certain pairs of adenine and guanine nucleotides give more than additive inhibition compared to the individual nucleotides, a phenomenon called synergistic inhibition. AMP plus GMP has been reported to be a strong synergistic nucleotide pair for the *E. coli* enzyme, although more recent experiments suggest that GDP plus AMP may be the most effective synergistic pair. The strongest synergistic pair for the *B. subtilis* enzyme has been reported to be ADP plus GMP.

The synergistic inhibition of glutamine PRPP amidotransferase implies the existence of separate binding sites for adenine and guanine nucleotides on each subunit. X-ray structures of *B. subtilis* and *E. coli* enzymes have identified four nucleotide binding sites per half-tetramer, two equivalent allosteric A sites between subunits, each with an adjacent catalytic C sites. It has been reported that synergistic binding of GMP to the A site and AMP to the C site could account for the synergistic inhibition of the *E. coli* enzyme.

A more systematic study of the mechanism for synergistic inhibition of the *B. subtilis* glutamine PRPP amidotransferase, as reported herein, confirms that ADP and GMP are the most synergistic pair and demonstrates that synergistic inhibition results from synergistic binding. An X-ray structure of a ternary enzyme ADP-GMP complex establishes that ADP binds to the A site and GMP to the C site and that synergism results from a specific interaction between the β-phosphate of a nucleoside diphosphate in the A site and a nucleoside monophosphate in the C site. These results establish the mechanistic basis for synergism.

SUMMARY OF THE INVENTION

Purine nucleotide production in bacteria is controlled and limited by regulation of gene expression as well as regulation of the enzymatic activity of pathway enzymes such as glutamine PRPP amidotransferase. This regulation limits production yields during commercial biosynthesis of inosine, as well as adenine and guanine nucleosides and nucleotides. Typically, commercial production of the nucleosides and nucleotides is carried out using Bacillus species that are genetically deregulated. However, due to feedback inhibition of glutamine PRPP amidotransferase, nucleotide overproduction in these genetically deregulated strains is less than maximal. The elimination, or at least the reduction, of nucleotide end-product inhibition of glutamine PRPP amidotransferase activity will further enhance the production yield of purine nucleotides.

In accordance with one embodiment of the present invention a modified glutamine PRPP amidotransferase is prepared that is desensitized to inhibition by purine nucleotides. The modified enzyme has at least one amino acid of the allosteric A sites or the catalytic C sites of said amidotransferase substituted with a non-native amino acid, wherein the substitution reduces the sensitivity of the enzyme to end product inhibition relative to the native glutamine PRPP amidotransferase enzyme. Furthermore, the present invention encompasses gene sequences that encode for the modified glutamine PRPP amidotransferase.

In accordance with one embodiment a method is provided for producing purine nucleotides. The method comprises the steps of culturing a host cell that comprises gene sequences encoding for a modified glutamine PRPP amidotransferase, wherein the modified glutamine PRPP amidotransferase has reduced sensitivity to end-product inhibition.

DETAILED DESCRIPTION OF THE INVENTION

Figure 1:
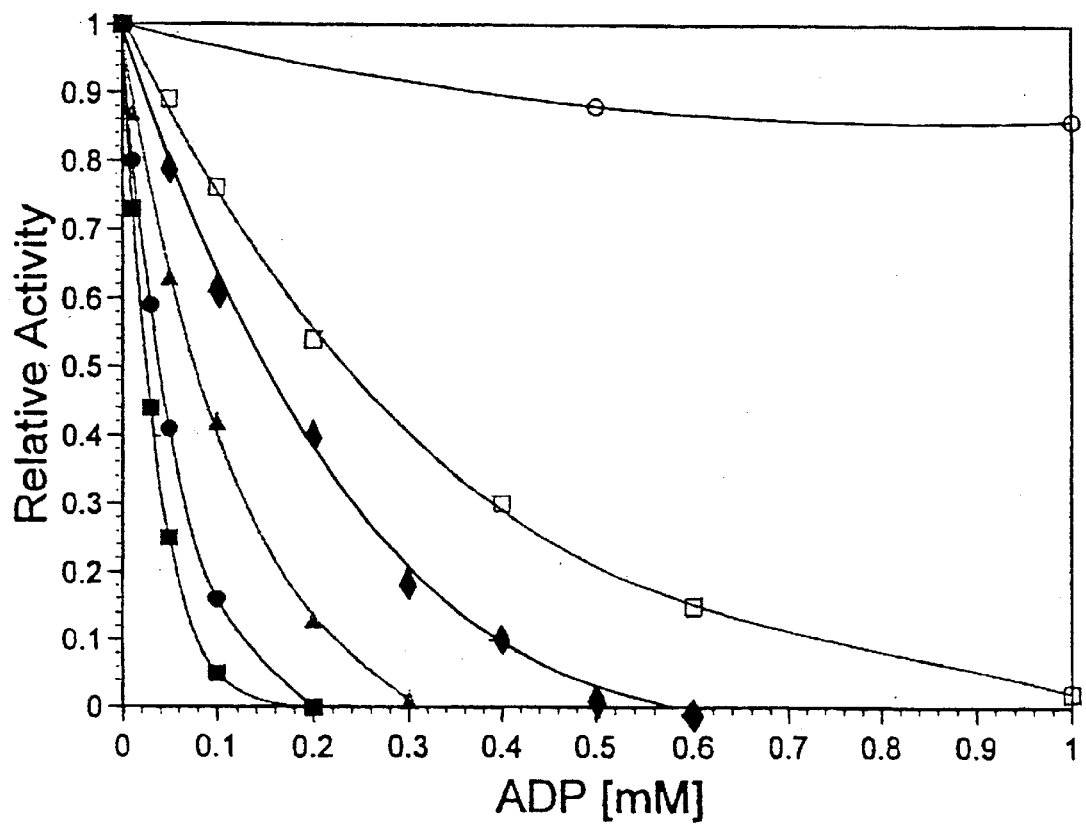
FIG. 1 is a graphic representation of the effect of different fixed concentrations of GMP on the inhibition of glutamine PRPP amidotransferase activity by ADP, wherein ■=4 mM GMP, ●=2 mM GMP, ▲=1.0 mM GMP, ♦=0.5 mM GMP, □=0.25 mM GMP, and ○=no GMP. At each of the six fixed GMP concentrations, the enzyme activity observed in the absence of ADP was assigned a relative activity of 1.0 and the inhibition by ADP was then determined.

A single pathway for de novo purine nucleotide synthesis results in the production of adenine and guanine nucleotides.

Uptake of either base or nucleoside can elevate the pool of the corresponding nucleotide and repress gene transcription by various different mechanisms. Commercial strains of bacteria have been prepared that are genetically deregulated to enhance the production of purine nucleotides. However, the enzymatic activity of the pathway enzyme glutamine PRPP amidotransferase is regulated based on the availability of both nucleotides. The interaction of adenine and guanine nucleotides with the A sites and the C sites determines the extent of inhibition of glutamine PRPP amidotransferase activity. Purine nucleoside mono- and diphosphates, AMP, GMP, and ADP, each bind to the A and C sites, however each of the sites has limited specificity, favoring certain nucleotides over others. For example, ADP and GMP preferably bind to the A and C sites, respectively, and for this nucleotide pair, there is minimal competition between nucleotides for each site. Feedback inhibition by one nucleotide is inefficient, and de novo synthesis continues until both nucleotides are in excess. When both nucleotides are bound to the enzyme a synergistic inhibitory effect on enzymatic activity is observed.

Synergistic inhibition of glutamine PRPP amidotransferase by particular nucleotide pairs enables cells to monitor and adjust the pools of adenine and guanine nucleotides, the end products of de novo biosynthesis. There are two key features of synergism. First, the inhibition by each nucleotide is amplified. AMP is the most potent single nucleotide inhibitor. However, as a consequence of synergism, an ADP/GMP mixture inhibits more strongly than AMP. Secondly, inhibition by one nucleotide is dependent upon the fixed concentration of the partner. Synergistic inhibition by the ADP-GMP nucleotide pair results from synergistic binding, and the synergistic binding results from an interaction between ADP in the A site and GMP in the C site. Finally, the synergistic effect is further amplified by the competition between PRPP and nucleotide for the C site.

The present invention relates to defining the structural features that dictate the binding of nucleotides to the A and C sites of glutamine PRPP amidotransferase and the resulting inhibition. Determination of the mechanism of nucleotide end-product inhibition has allowed the construction of modified glutamine PRPP amidotransferases that are desensitized to inhibition by purine nucleotides. The native glutamine PRPP amidotransferase is modified in accordance with the present invention by substituting one or more the amino acids within the A site or C site peptide domains with different amino acids that result in decreased sensitivity of the modified enzyme to end-product inhibition. Such modified enzymes have been shown to have normal catalytic function in vitro and in vivo but are less sensitive to nucleotide inhibition.

In accordance with this invention there is provided a novel glutamine PRPP amidotransferase having a reduced sensitivity to inhibition by adenine and guanine nucleotides. Any mutation of the native glutamine PRPP amidotransferase that decreases the ability of the enzyme to bind to adenine and guanine nucleotides will result in increased nucleotide concentration being required to inhibit glutamine PRPP amidotransferase activity. Thus higher basal levels of purine nucleotides will accumulate in strains that encode the modified glutamine PRPP amidotransferase.

In one embodiment, the modified glutamine PRPP amidotransferase has at least one amino acid of the allosteric A sites or the catalytic C sites of the amidotransferase modified, wherein the modification reduces end product inhibition of the glutamine PRPP amidotransferase enzymatic activity by adenine or guanine nucleotides. Amino acid positions within the A and C site peptide domains that participate in hydrogen bonding with the inhibitory nucleotides, and amino acids that interact with the complexed $Mg^{2+}$, are preferred amino acid positions for modification (including deletion, addition or substitution of amino acids). Preferably the enzyme is modified by substituting one or more amino acids of the allosteric A sites or the catalytic C sites with amino acids that decrease binding of adenine and/or guanine nucleotides at the A sites or C sites. In one preferred embodiment the native amino acids are substituted with amino acids similar in structure to the substituted native amino acid (for example, substituting serine with alanine or substituting lysine or arginine with glutamine). Such substitutions remove ligands involved in nucleotide binding and thus impair binding to the enzyme (and therefore reduce end-product inhibition) while minimizing the impact on overall enzymatic activity.

In one embodiment, one or more of amino acid positions 242, 244, 282, 283, 305, 307, 345, 346, 347 and 350 of *Bacillus subtilis* amidotransferase, or at the equivalent positions in homologous enzymes, are substituted with non-native amino acids to form a modified glutamine PRPP amidotransferase. In homologous enzymes these amino acids may have different numbers, but will occupy a similar position within the A site and C site peptide domains of the enzyme. Preferably the modifications disrupt the synergistic binding of adenosine and guanine nucleotides to the amidotransferase.

Preferred glutamine PRPP amidotransferase proteins for modification are selected from the group of *E. coli* and *Bacillus subtilis* amidotransferases. In one embodiment the a Bacillus glutamine PRPP amidotransferase is modified to have a non-native amino acid at an amino acid position selected from the group consisting of 283, 305, 307 or 347, wherein said amino acid modification reduces the sensitivity of the modified glutamine PRPP amidotransferase end product inhibition relative to the native Bacillus PRPP amidotransferase.

The modified glutamine PRPP amidotransferases are prepared in accordance with one embodiment by mutating the gene encoding the native enzyme using techniques known to those skilled in the art. The entire sequence of the *E. coli* and *Bacillus subtilis* glutamine PRPP amidotransferases have been determined and are reported in *J. Biol Chem.* 257, 3525–3531 (1982), *Nucleic Acids Res.* 16, 8717 (1988) and *J. Biol. Chem.* 258, 10586–10593, respectively, the disclosures of which are expressly incorporated herein. Preferably the native gene is mutated through the use of recombinant nucleic acid technology, and more particularly through the use of site directed mutagenesis.

In accordance with the present invention, a nucleic acid sequence is provided that encodes for a glutamine PRPP amidotransferase that is desensitized to inhibition by purine nucleotides. In one preferred embodiment the nucleic acid sequences encoding the A site and C site peptide domains are modified to encode for non-native amino acids at one or more sites within these two peptide domains. The modifications to the glutamine PRPP amidotransferase gene reduce synergistic binding of adenine and guanine nucleotides to the expressed enzyme species and thus the modifications desensitize the enzyme to inhibition by purine nucleotides.

In accordance with one embodiment, a method is provided for enhancing the production of purine nucleotides in a host cell. The method comprises the steps of transforming a host cell with recombinant DNA encoding a glutamine PRPP amidotransferase modified in accordance with the present invention, and culturing the transformed host cell. The purine nucleotide products are then harvested from the proliferating population of recombinant host cells using standard recovery and purification procedures known to those skilled in the art.

The nucleic acid sequences of the present invention can be introduced into a host cell by plasmids, cosmids, phages, yeast artificial chromosomes or other vectors that mediate transfer of the genetic elements into a host cell. These vectors can include an origin of replication along with cis-acting control elements that control replication of the vector and the genetic elements carried by the vector. In one embodiment the modified gene is operably linked to a strong constitutive promoter. A constitutive promoter is one that transcribes a gene at a constant rate during the life of a cell and thus is not subject to regulation. Selectable markers can be present on the vector to aid in the identification of host cells into which the genetic elements have been introduced. For example, selectable markers can be genes that confer resistance to particular antibiotics such as tetracycline, ampicillin, chloramphenicol, kanamycin, or neomycin. The nucleic acids introduced into the host cell can be either chromosomal (e.g. integrated into a host cell chromosome) or extrachromosomal (e.g. carried by plasmids, cosmids, etc).

In accordance with one embodiment, the means for introducing genetic elements into a host cell utilizes an extrachromosomal multi-copy plasmid vector into which glutamine PRPP amidotransferase gene is inserted using techniques known to those skilled in the art. Plasmids suitable for insertion of genetic elements into the host cell include but are not limited to pBR322, and its derivatives such as pAT153, pXf3, pBR325, pBr327, pUC vectors, pACYC and its derivatives, pSC101 and its derivatives, and ColE1. In addition, cosmid vectors such as pLAFR3 are also suitable for the insertion of genetic elements into host cells.

Preferred plasmid constructs comprising a modified glutamine PRPP amidotransferase gene include but are not limited to pBsF/S283A (wherein a serine at position 283 is substituted with alanine), pBsF/K305Q (wherein a lysine at position 305 is substituted with glutamine), pBsF/R307Q (wherein a arginine at position 307 is substituted with glutamine), and pBsF/S347A (wherein a serine at position 347 is substituted with alanine).

Host cells suitable for use in the present invention are members of those genera capable of being utilized for industrial biosynthetic production of desired purine nucleotides. Host cells including purine nucleotide pathways of this type include prokaryotes belonging to the genera Escherichia, Klebsiella, Corynebacterium, Brevibacterium, Arthrobacter, Bacillus, Pseudomonas, Streptomyces, Staphylococcus, or Serratia. Eukaryotic host cells can also be utilized, with yeasts of the genus Saccharomyces or Schizosaccharomyces being preferred.

More specifically, prokaryotic host cells are derived from species that include *Escherichia coli, Klebsiella pneumonia, Corynebacterium glutamicum, Corynebacterium herculis, Brevibacterium divaricatum, Brevibacterium lactofermentum, Brevibacterium flavum, Bacillus brevis, Bacillus cereus, Bacillus circulans, Bacillus coagulans, Bacillus lichenformis, Bacillus megaterium, Bacillus mesentericus, Bacillus pumilis, Bacillus subtilis, Pseudomonas aeruginosa, Pseudomonas angulata, Pseudomonas fluorescens, Pseudomonas tabaci, Streptomyces aureofaciens, Streptomyces avermitilis, Streptomyces coelicolor Streptomyces griseus, Streptomyces kasugensis, Streptomyces lavendulae, Streptomyces lipmanii, Streptomyces lividans, Staphylococcus epidermis, Staphylococcus saprophyticus*, or *Serratia marcescens*. In particular, commercial bacterial strains currently used to produce purine nucleotides are one preferred set of bacterial host cells suitable for use in accordance with the present invention, and more particularly, commercial cell line that have been altered to remove the genetic regulation of the glutamine PRPP amidotransferase gene.

The modified glutamine PRPP amidotransferase is expressed in the host cell simultaneously with the native gene, or alternatively, the native gene is inactivated or removed prior to transformation. In one embodiment the native gene is replaced with the gene encoding the modified glutamine PRPP amidotransferase through a homologous recombination event. Disabling the native gene by insertion of the recombinant gene encoding the modified glutamine PRPP amidotransferase advantageously allows for incorporation of the modified gene into the genome and ensures that the only expressed glutamine PRPP amidotransferase enzyme is one that has reduced sensitivity to inhibition by adenine and guanine nucleotides.

EXAMPLE 1

Characterization of the Site A and Site B Binding Sites

The following experiments were conducted to characterize and define the structural features that dictate the binding of nucleotides to glutamine PRPP amidotransferase and result in the inhibition of enzymatic activity.

Plasmids.

Plasmid pGZ1 was used for production of the wild type enzyme. Plasmid pGZ1 contains a 1.6 kb EcoRI-HindIII purF+ fragment (Makaroff, C. A., Zalkin, H., Switzer, R. L., and Vollmer, S. J. (1983) *J. Biol. Chem.* 258, pp. 10586–10593) inserted into the corresponding sites of pUC18. For construction of mutants, the EcoRI-HindIII purF+ DNA was transferred to pUC118 to yield pBsF. Mutations were constructed by the method of Kunkel et al. (Kunkel, T. A., Roberts, J. D., and Zakour, R. A. (1987) *Methods Enzymol.* 154, pp. 367–382) using pBsF phagemid DNA. The resulting plasmids were named pBsF/S283A, pBsF/K305Q, pBsF/R307Q, and pBsF/S347A.

Overexpression and Enzyme Purification.

*E. coli* strain TX158 (purF) bearing the wild type or purF mutant plasmid was grown in minimal medium plus 140 $\mu$g/mL ampicillin at 37° C. for 20 h. Cells were harvested and stored in liquid nitrogen. For a typical purification, we used 10 g of cells obtained from 4 L of medium.

For enzyme purification, all buffers were sparged with nitrogen gas prior to use in order to minimize oxidation of the enzyme's Fe-S cluster. All steps were carried out at 4° C. Cells were resuspended in 4 mL/gram of buffer A [50 mM Tris-HCl (pH 8.0), 10 mM $MgCl_2$, 0.1 mM EDTA, 5 mM DTT, and 2 mM AMP] containing 1 mM PMSF, and were disrupted by two passes through a French Press. The cell extract was obtained by centrifugation for 1 h at 27,000 g. Protamine sulfate (5 mg per gram of cells) was added to the extract to precipitate DNA. After centrifugation at 27,000 g for 30 min, the supernatant was applied to a 1.9×20 cm column of DEAE-Sepharose equilibrated with buffer A. The column was washed with 300 mL of buffer A and 300 mL of buffer A plus 0.1 M KCl and eluted with a linear salt gradient of 600 mL from 0.1 to 1.0 M KCl in buffer A. Brown-colored fractions containing the enzyme were precipitated by addition of ammonium sulfate to 40% saturation. After centrifugation, enzyme in the brown pellet was recovered by extraction twice with 30% saturated ammonium sulfate. A small colorless pellet that remained was discarded, and the dark brown enzyme solution in buffer A containing residual ammonium sulfate was stored as beads in liquid nitrogen. Enzyme purity was estimated to be approximately 95% by sodium dodecyl sulfate-polyacrylamide gel electrophoresis. Enzyme specific activity was typically 25 nmol min$^{-1}$ mg$^{-1}$ for the wild type and 17–34 nmol min$^-$ mg$^-$ for the mutants. For assays of activity, the enzyme was diluted 1:1000 in 50 nM Tris-HCl (pH 8.0) containing 1 mg/mL bovine serum albumin. For measurements of ligand binding by equilibrium dialysis and for crystallization experiments, the enzyme was dialyzed anaerobically against buffer B [50 mM Tris-HCl (pH 8.0), 0.1 mM EDTA, and 5 mM DTT] prior to being used.

Enzyme Assay

Enzyme activity was assayed by measuring the initial rate of formation of the product glutamate. The standard assay contained 2.5 mM PRPP, 20 mM glutamine, 10 mM MgCl$_2$, 1 mM EGTA, 1 mg/mL bovine serum albumin, 50 mM Tris-HCl (pH 8.0) and approximately 100 ng of enzyme in a total volume of 100 µL. Incubation was at 37° C. for 6 min. The reaction was linear with time for at least 20 min under these conditions of assay. Reactions were quenched in a boiling water bath for 2 min, and glutamate was determined by the glutamate dehydrogenase method. The control reaction mixture contained all the components except PRPP.

Inhibition by nucleotides was determined by the standard assay to which varied concentrations of nucleotide were added. Synergistic inhibition was determined by varying the concentration of one nucleotide in the presence of a fixed concentration of a second nucleotide. Relative activity (see FIG. 1) refers to the enzyme activity at a given concentration of the varied nucleotide relative to that in the absence of the varied nucleotide. $I_{0.5}$ values were calculated from plots of relative activity versus varied nucleotide concentration.

Nucleotide Binding.

Nucleotide binding was determined by equilibrium dialysis using chambers of 150 µL that were separated by a 12000–14000 molecular weight dialysis membrane. One chamber contained 0.2 M Tris-HCl (pH 7.5), 20 mM MgCl$_2$, and varied concentrations of a radioactive nucleotide (0–20 mM [2,8-$^3$H]AMP, [8-$^3$H]GMP, [2,8-$^3$H]ADP, or [8-$^4$C] IMP, approximately 0.1 µCi in each case) in a volume of 100 µL. In some experiments, the chambers with radioactive nucleotide also contained a fixed concentration of a second non-radioactive nucleotide. The other chamber contained 50 mM Tris-HCl (pH 7.5) and 50–200 µM enzyme, calculated as the subunit concentration, in a volume of 100 µL. Dialysis was carried out for 20 h at room temperature (~22° C.) in a rotating apparatus. Samples of 80 µL were retrieved from each chamber and were counted for radioactivity. All experiments were performed in an anaerobic glovebox. For all data reported in Table 2, there was less than 10% activity loss at the conclusion of dialysis. Equilibrium binding data were fit to the Hill equation (Y=C [free ligand]$^n$/1K$_d$+[free ligand]$^n$, where Y is the fractional saturation, C is the binding capacity, K$_d$ is the dissociation constant, and n is the Hill coefficient) by nonlinear regression using Ultrafit software (Biosoft, Cambridge, UK).

Crystallization and Structure Solution.

Crystals of the ternary enzyme-ADP-GMP complex were grown in glass melting point capillaries by the microbatch method in an anaerobic glovebox. Protein (20 mg/ML) was incubated with 1 mM ADP, 1 mM GMP, and 5 mM MgCl$_2$ and mixed with an equal volume of 24% PEG 8000, 200 mM KCl, 50 mM N-(2-hydroxyethyl)piperazine-N-3-propanesulfonic acid (EPPS, pH 7.9), 1 mM ADP, 1 mM GMP, and 5 mM MgCl$_2$. Brown crystals grew to a typical dimension of 0.8×0.5×0.5 mm over a period of 6–12 weeks. Crystals were cryoprotected for flash freezing by serial transfer, in steps of 5% glycerol, into a cryoprotectant solution of 25% glycerol, 16% PEG 8000, 200 mM KCl, 50 mM EPPS (pH 7.9), 1 mM ADP, 1 mM GMP, and 5 mM MgCl$_2$, in a sitting drop well. The well was sealed with clear plastic tape and removed from the glovebox, and the crystals were rapidly mounted in a small plastic fiber loop and frozen in a nitrogen gas stream at 120K. No change in color or diffraction quality of the crystals due to oxygen exposure was observed during this procedure.

X-ray diffraction data to a $d_{min}$ of 2.8 Å were collected from a single crystal, flash frozen to 120K with an Oxford Cryostream, using an R axis II imaging plate system mounted on a Rigaku RU-200 rotating anode (CuKα) operated at 100 mA and 50 kV. Crystals of the 465-residue enzyme grew in the orthorhombic space group P2$_1$2$_1$2$_1$ (α=160.3 Å, b=70.4 Å, and c+182.7 Å), with a homotetramer of approximate D2 point symmetry in the asymmetric unit. The data were processed and scaled in the programs DENZO and Scalepack (Otwinowski, Z. (1993) in Data Collection and Procedssing (Sawyer, N. I. L., and Bailey, S., Eds.) pp. 56–62, Science and Engineering Research Council Daresbury Laboratory, Daresbury, UK); data processing statistics are shown in Table 1.

A 2.3 Å model of the AMP-inhibited native B. subtilis glutamine PRPP amidotransferase was previously refined using data measured from unfrozen crystals. This structure without the AMP nucleotides was used as an initial model for the ternary enzyme-ADP-GMP complex, which crystallizes isomorphously. All refinement was done with X-PLOR (Brunger, A. T. (1992a) XPLOR Version 3.1, A System for X-ray Crystallography and NMR, Yale University Press, New Haven, Conn.). Rigid-body refinement of the independent monomers of the tetramer resulted in an R-factor of 36.4% for data between 12.0 and 2.8 Å; inspection of the resulting electron density maps using the program O (Jones, T. A., Zou, J. Y., Cowan, S. W., and Kjeldgaard, M. (1991) Acta Crystalloger. A.47, pp. 110–119) revealed density for the ADP, GMP, and Mg$^{2+}$ bound to the protein. The density clearly distinguished binding sites for ADP and GMP. Subsequent refinement against data from 15.0 to 2.8 Å spacings utilized a test set of 5% of the reflections for R$_{free}$ calculations and a bulk solvent mask. Simulated-annealing refinement with strict non-crystallographic symmetry constraints yielded an R$_{free}$ of 30.8% and an R$_{work}$ of 26.0%. Conventional positional and grouped β-factor refinement of the tetramer with tightly restrained noncystallographic symmetry was employed with a Bayesian weighting scheme for structure factors as implemented in the program HEAVY (Terwiller, T. C., and Berendzen, J. (1995) Acta Crystallogr. D 51, pp. 609–618). A summary of refinement statistics is presented in Table 1.

TABLE 1

Data and Refinement Statistics

| data | |
| --- | --- |
| resolution range (Å) | 15.0–2.8 |
| no. of observations | 195 956 (40.0–2.8Å) |

TABLE 1-continued

Data and Refinement Statistics

| | |
|---|---|
| no. of unique reflections | 46 771 |
| completeness (%) (15.0–2.8Å) | 91.0 |
| $R_{sym}(\%)^a$ (40.0–2.8Å) | 8.0 |
| model refinement | |
| missing residues | 76–79, 460–465 for each monomer |
| total non-hydrogen atoms | 14 156 |
| no. of non-protein atoms in model | |
| $Mg^{2+}$ sites | 4 |
| water sites | 4 |
| nucleotides | 4 GMP plus 2 ADP |
| data range | 15.0–2.8Å |
| cutoff[Flσ(F)] | 0.0 |
| $R_{work}(\%)^b$ | 21.4 |
| $R_{free}(\%)^c$ | 26.4 |
| mean B value (Å) | |
| main chain | 30.8 |
| side chain | 36.0 |
| rms deviations from ideality | |
| bonds (Å) | 0.016 |
| angles (deg) | 2.50 |
| B values ($Å^2$) | |
| main chain | 2.97 |
| side chain | 4.70 |
| noncrystallographic symmetry (Å) | 0.19 |
| Ramachandran outliers | none |

$^a R_{sym} = \Sigma |I_o-(I)|/I_o$ is the observed intensity and (I) is the average intensity obtained from multiple observations of symmetry related reflections.
$^b R_{work} = \Sigma| |F_{obs}| - |F_{calc}||\Sigma|F_{obs}|$, where $F_{obs}$ is the observed structure factor and $F_{calc}$ is the structure factor calculated from the final model. The value quoted included all of the reflections, including the ones used for the $R_{free}$ calcuation.
$^c r_{free} = \Sigma| |F_{obs}| - |F_{calc}||\Sigma|F_{obs}|$ for a random subset of 5% of the total reflections collected.

Results

Structures of Enzyme Sites with Bound Nucleotides.

Earlier work showed that the strongest synergistic pair of nucleotide inhibitors for *B. subtilis* glutamine PRPP amidotransferase is ADP plus GMP. In order to understand the structural basis for the nucleotide specificity and synergism, the X-ray crystal structure of the ternary enzyme-ADP-GMP complex was determined. Data and refinement statistics are given in Table 1. ADP and GMP bind to sites identified previously as AMP binding sites in the AMP-inhibited enzyme. Each functional dimer of the amidotransferase contains two catalytic C sites and two allosteric A sites, which are located near the subunit interface. Electron density for the nucleotides clearly demonstrates that GMP binds to the C sites and ADP to the A sites, with no detectable exchange of nucleotides between the two sites.

Residues 341–353 of the C site contain a PRPP-binding sequence motif common to type I phosphoribosyltransferases (type I PRTases). This motif forms a hydrophobic β-strand, the PRPP loop itself, which typically contains two acidic residues ($Asp^{345}$ and $Asp^{346}$), and the first turn of an α-helix. As in the AMP-inhibited structure, the 5'-phosphate of GMP in this site binds to the $NH_2$ terminus of the α-helix with hydrogen bonds to backbone amides of the PRPP loop and to the side chain of $Arg^{350}$. A $Mg^{2+}$ is coordinated to the GMP ribose 2'-and 3'-hydroxyls, to the side chain carboxylate oxygens of $Asp^{345}$ and $Asp^{346}$ in the PRPP loop, to the hydroxyl of $Ser^{283}$, and to an $H_2O$ molecule. The $Mg^{2+}$ was not detected in the 3.0 Å AMP-inhibited structure but was located in the refined 2.3 Å structure in the same coordination environment. In contrast to the adenine base in the AMP-inhibited structure which binds in the usual anti conformation, the guanine base of GMP binds in the syn conformation, which is stabilized by a hydrogen bond between the 2-$NH_2$ group of the guanine and the hydroxyl of $Ser^{347}$.

Each of the two allosteric A sites at the dimer interface binds an ADP molecule. Binding results from interactions with residues in both subunits. From the primary subunit, there are hydrogen bonds between the backbone carbonyls of $Tyr^{242}$ and $Ser^{244}$ with the 3'-and 2'-hydroxyls, respectively, of the ribose moiety and the $\in$-$NH_2$ of $Lys^{305}$ with the ADP α-phosphate. The $\in$-$NH_2$ of $Lys^{305}$ is also salt bridged to the carboxylate of the $Asp^{282}$. Interactions with the secondary subunit occur through the side chain of $Arg^{307'}$, which hydrogen bonds to the α-phosphate of the ADP, and the backbone carbonyl of $Lys^{305'}$. The $Lys^{305'}$ carbonyl hydrogen bonds to the 6-$NH_2$ group of the adenine base and is responsible for base specificity in the A site which favors purines with a 6—$NH_2$ group over those with a 6-oxo group. The contribution of amino acid residues from two adjacent subunits to A site nucleotide binding should account, at least in part, for the positive cooperativity of nucleotide inhibition.

Inhibitor binding sites in other allosteric enzymes are distant from the active sites and are typically between subunits. Glutamine PRPP amidotransferase differs from the typical case because the A and C sites are adjacent. Direct contact between the sites occurs via a hydrogen bond between the β-phosphate of ADP in the A site and the ribose 2'-OH of GMP in the C site. This is proposed to be the structural basis for synergistic binding and inhibition by ADP plus GMP.

An unusual cis peptide has been observed in a loop adjacent to the C site of all high-resolution glutamine PRPP amidotransferase structures and appears to have a functional role in inhibition. Density for this peptide in the ADP-GMP complex is also consistent with a cis conformation. An ADP α-phosphate oxygen is hydrogen bonded to the backbone NH of the cis peptide in the $Pro^{281}$-cis-$Asp^{282}$-$Ser^{283}$ turn. Thus, the cis conformation seems to be required for inhibition and synergism. The cis peptide is also likely to have a role in binding the substrate PRPP or in catalysis because it has also been observed in an analogous position in other type I PRTases. A hydrogen bond from NH of the cis peptide to the β-phosphate of substrate PRPP would be analogous to the observed hydrogen bond to ADP.

Analysis of Nucleotide Binding.

Equilibrium binding measurements, summarized in Table 2, were carried out to quantitate the interactions of nucleotides with the A and C sites. Binding of AMP and ADP extrapolated to 1.57 and 1.83 equiv per subunit, respectively. Thus, AMP and ADP each bound to both the A and C sites. As a consequence of cooperativity, nucleotide binding was analyzed by the Hill equation rather than by the Scatchard equation. Apparent $K_d$ values and Hill coefficients for AMP and ADP are given in Table 2. Apparent $K_d$ values of 239 and 214 μM for AMP and ADP, respectively, are not true dissociation constants but are equivalent to nucleotide concentrations required for half-saturation of the two sites of each subunit. GMP binding, on the other hand, was too weak to detect, indicative of a $K_d$ greater than approximately 0.5 mM. The Hill coefficient of 3.4 for binding of AMP agrees closely with values of 3.3–3.8 determined from inhibition data. However, the Hill coefficient for ADP binding of 1.8 is less than the value of 3.8 determined from inhibition data. It is possible that PRPP, present in the assay for inhibition but not in binding measurements, accounts for this difference.

Competition between PRPP and adenine nucleotides for the C site is an important factor in the inhibition by AMP and ADP.

Binding of AMP, ADP, and GMP was also determined in the presence of a fixed concentration of a second nucleotide in order to quantitate synergistic binding. The ADP-GMP pair exhibited the strongest binding synergism. With GMP fixed at either 0.25 or 1.0 mM, approximately 1 equiv of ADP was bound with a $K_d$ of about 10 µM (Table 2, lines 4 and 5). The binding of ADP was thus independent of the fixed concentration of GMP under the conditions used. For the reciprocal case, 1 equiv of GMP was bound to the C site with a $K_d$ of 25 µM in the presence of 0.5 mM ADP (Table 2, line 6). For the GMP-ADP pair, one nucleotide strongly enhanced the binding of the other as can be seen by comparison of these data with the average apparent $K_d$ values for the individual nucleotides shown in lines 2 and 3 of Table 2. This estimate for synergistic binding is greater than 20-fold for the GMP-ADP pair; i.e., $K_d$ AMP decreased from 214 to 10 µM and $K_d$AMP from >500 to 25 µM.

The crystal structure of the ternary enzyme-ADP-GMP complex shows that strong synergistic binding of the ADP-GMP pair arises from ADP binding to the A site and GMP binding to the C site and from a direct hydrogen bond between the nucleotides bond in these two sites. Synergistic binding is enhanced by exclusion of each nucleotide from the site to which it does not bind. A base-specific hydrogen bond in the A site likely discriminates against GMP in this site. While ADP is not excluded from the C site, the salt bridge between the GMP 5'-phosphate and $Arg^{350}$ is specific for nucleoside monophosphates and the hydrogen bond between guanine $2-NH_2$ and $Ser^{347}$ is specific to syn purines with an exocyclic 2-position substituent.

TABLE 2

NUCLEOTIDE BINDING TO THE WILD TYPE ENZYME

| Nucleotide | | | | |
|---|---|---|---|---|
| Varied | Fixed$^a$(mM) | Capacity$^b$ | $K_d$(µM) | Hill coefficient |
| AMP | | 1.57 ± 0.27 | 239 ± 36 | 3.4 ± 1.8 |
| ADP | | 1.83 ± 0.26 | 214 ± 45 | 1.8 ± 0.65 |
| GMP | | ND$^c$ | ND | ND |
| ADP | GMP (0.25) | 0.82 ± 0.11 | 10.4 ± 2.7 | 1.8 ± 0.8 |
| ADP | GMP (1.0) | 0.94 ± 0.14 | 11.0 ± 3.6 | 1.7 ± 0.9 |
| GMP$^d$ | ADP (0.5) | 0.98 ± 0.10 | 25 ± 12 | 2.1 ± 1.0 |
| AMP | GMP (1.0) | 1.05 ± 0.21 | 103 ± 21 | 2.1 ± 0.80 |
| AMP | ADP (0.25) | 0.94 ± 0.16 | 77 ± 21 | 2.3 ± 1.2 |
| IMP | ADP (0.25) | 0.99 ± 0.22 | 68 ± 27 | 1.8 ± 1.0 |

$^a$The millimolar concentration of fixed nucleotide is given in parentheses.
$^b$Equivalents bound per subunit at saturation ± standard error.
$^c$ND$_1$ not detected $K_d$> 0.5 mM.
$^d$Similar binding in the presence of 0.25 mM ADP (now shown).

Binding of nucleotide pairs involving AMP is more complex because AMP binds effectively at both the A and C sites. Binding of AMP was determined in the presence of a fixed concentration of either GMP or ADP. Data in Table 2 (lines 7 and 8), indicate binding of approximately 1 equiv of AMP per subunit with similar $K_d$ values of 77 or 103 µM in the presence of ADP or GMP, respectively. With these nucleotide combinations, it is more difficult to assign the site to which AMP bound, because nucleoside monophosphates compete for the C site and adenine nucleotides compete for the A site. For example, when the fixed concentration of ADP was increased from 0.25 to 0.5 mM, the AMP binding stoichiometry was decreased to approximately 0.4 equiv/subunit with a $K_d$ of ~300±500 µM, indicative of weak binding due to the A site competition (data not shown). It is thus reasonable to infer that AMP binds predominantly to the C site in the presence of ADP and predominantly to the A site in the presence of GMP. Irrespective of the assignment of binding sites, there was only limited synergism for the AMP-GMP and AMP-ADP pairs. The binding affinity for AMP was increased 2–3-fold by GMP or ADP.

To evaluate the importance of the $Ser^{347}$ interaction with the amino group at position 2 of the purine ring with regard to C site binding of nucleotides, binding was determined for IMP, which lacks the 2-amino groups, but is otherwise identical to GMP. With ADP bound to the A site, 1 equiv of IMP was bound to the C site with a $K_d$ of 68 µM (Table 2). Thus, the $Ser^{347}$ interaction with the 2-amino group of GMP results in a 3-fold increased binding affinity.

Synergistic Inhibition of the Wild Type Enzyme by Nucleotides.

Previous work established the following order for effectiveness of nucleotide inhibitors; AMP>ADP>GDP>GMP. We determined values for 50% inhibition by AMP, ADP, and GMP (Table 3) that agreed closely with the earlier work. It is important to note that the concentration of ADP required for 50% inhibition is 5 times that for AMP yet apparent binding constants for AMP and ADP shown in Table 2 are similar. This discrepancy is believed to result from the different conditions used to measure inhibition and nucleotide binding. The concentration of GMP required for 50% inhibition was 2- and 10-fold higher than that of ADP and AMP, respectively. This is in accord with the weaker binding of GMP relative to the adenine nucleotides, shown in the first three lines of Table 2. The $I_{0.5}$ for IMP was 3-fold higher than that for GMP.

Two methods have been used previously to quantitate synergistic inhibition of glutamine PRPP amidotransferase by nucleotides. In one method, the observed $I_{0.5}$ for an equimolar nucleotide mixture was compared with the value calculated for additive inhibition by each nucleotide of the pair. A second approach has been to compare the observed inhibition by arbitrary concentrations of nucleotide pairs with that calculated for additive inhibition. For this work, we have developed a more systematic method for quantitating synergism by nucleotide pairs. For a given nucleotide pair, ADP-GMP for example, the $I_{0.5}$ for one member was determined in the presence of a fixed concentration of the other. Enzyme inhibition by ADP, determined in the presence of different fixed concentrations of GMP, is shown in FIG. 4. An $I_{0.5\ ADP}$ of 0.24 mM was obtained at a fixed GMP concentration of 0.25 mM (Table 3). Thus, binding of GMP to the C site reduced the $I_{0.5\ ADP}$ from 4.7 mM (no GMP) to 0.24 mM, a 20-fold synergism.

As shown in FIG. 4 and Table 3, the inhibition by ADP, and therefore the synergism, are dependent upon the concentration of the fixed nucleotide. $I_{0.5\ ADP}$ varied 10-fold depending upon the fixed GMP concentration. This is due to completion between PRPP and GMP for the C site. The competitive relationship between PRPP saturation and nucleotide inhibition has been described for the B. subtilis enzyme. To standardize comparisons of different nucleotide pairs with wild type and standardize comparisons with mutuant enzymes, synergism was calculated using a fixed nucleotide concentration set to approximately 0.1 of its $I_{0.5}$ when assayed individually. Accordingly, at a fixed concentration of 1.0 mM GMP, the $I_{0.5}$ ADP was 0.08 mM with 59-fold synergism (0.08 versus 4.7 mM). For the reciprocal case, titration of GMP at a fixed concentration of 0.5 mM ADP (approximately 0.1 of the $I_{0.5\ ADP}$ of 4.7) gave an $I_{0.5\ GMP}$ of 0.15 mM and 63-fold synergism (0.15 versus 9.4 mM). The average value for synergism of the ADP-GMP pair is therefore 61. For the ADP-IMP pair, synergism was 28. By contrast, the average synergism for the AMP-ADP pair was 1.7, and there was no synergism for the AMP-GMP pair.

for a nucleoside diphosphate in the C site. Without rearrangement of residues in the PRPP loop, there is insufficient space for the β-phosphate of a nucleoside diphosphate. Nevertheless, ADP was bound to both sites with a value for

TABLE 3

SUMMARY FOR INHIBITION OF WILD TYPE AND MUTANT ENZYMES BY NUCLEOTIDES

| nucleotide | | wild type | | S283A | | K305Q | | R307Q | | S347A | |
|---|---|---|---|---|---|---|---|---|---|---|---|
| varied | fixed[a] | $I_{0.5}$(mM) | syn.[b] | $I_{0.5}$(mM) | syn. | $I_{0.5}$(mM) | syn. | $I_{0.5}$(mM) | syn. | $I_{0.5}$(mM) | syn. |
| AMP | | 0.9 | | 6.1 | | 2.5 | | 2.6 | | 1.5 | |
| ADP | | 4.7 | | 24.0 | | 31.0 | | 28.0 | | 8.1 | |
| GMP | | 9.4 | | 6.6 | | 50.0 | | 50.0 | | 14.0 | |
| IMP | | 26.0 | | | | | | | | 41.0 | |
| ADP | GMP (0.25) | 0.24 | 20.0 | | | | | | | | |
| ADP | GMP (0.50) | 0.16 | 29.0 | 4.8 | 5.0 | 12.0 | 2.6 | 2.4 | 12.0 | | |
| ADP | GMP (1.0) | 0.08 | 59.0 | | | | | | | $0.22^c$ | 37.0 |
| ADP | GMP (2.0) | 0.04 | 118.0 | | | | | | | | |
| ADP | GMP (4.0) | 0.025 | 188.0 | | | | | | | | |
| ADP | GMP (5.0) | | | | | 0.32 | 97.0 | 0.18 | 156.0 | | |
| GMP | ADP (0.5) | 0.15 | 63.0 | 2.0 | 3.3 | 6.0 | 8.3 | 3.3 | 15.0 | $0.44^c$ | 33.0 |
| GMP | ADP (2.5) | | | 1.7 | 3.9 | 1.3 | 38.0 | 0.76 | 66.0 | | |
| IMP | ADP (0.5) | 0.93 | 28.0 | | | | | | | $1.6^c$ | 26.0 |
| AMP | ADP (0.5) | 0.64 | 1.4 | | | | | | | $0.65^c$ | 2.3 |
| AMP | GMP (1.0) | 0.94 | 1.0 | | | | | | | $1.8^c$ | 0.8 |
| GMP | AMP (0.1) | 9.9 | 0.95 | | | | | | | | |
| ADP | AMP (0.1) | 2.5 | 1.9 | | | | | | | | |

[a]The millimolar fixed nucleotide concentration is in parentheses.
[b]Decreased $I_{0.5}$ due to a second nucleotide. The concentration of the second nucleotide was approximately 0.1 of its individual $I_{0.5}$.
[c]Fixed nucleotide concentrations were 1.4 mM GMP and 0.8 mM ADP rather than the values shown in column 2.

Discussion

Analysis of the binding of adenosine and guanine nucleotides to the A and C sites of glutamine PRPP amidotransferase indicates that:

(i) Each of the sites has limited specificity, favoring certain nucleotides over others,
(ii) Synergistic inhibition by the ADP-GMP nucleotide pair results from synergistic binding,
(iii) Synergistic binding results from an interaction between ADP in the A site and GMP in the C site,
(iv) Competition between PRPP and nucleotide for the C site amplifies synergism and explains the more effective inhibition of AMP compared to that of ADP.

Specificity of Nucleotide Sites.

The x-ray structural model of the nucleotide A and C sites for the ternary ADP-GMP-enzyme complex, together with the structure of the AMP complex, explains the adenine nucleotide specificity for the A site and GMP specificity for the C site. The specificities result mainly from base-specific H bonds between the Lys[305] backbone oxygen and the adenine 6-amino group in the A site and between the Ser[47] hydroxyl and the guanine 2-amino group in the C site. The adenine-specific hydrogen bond in the A site discriminates against other nucleotides in this site, which can accommodate only the anti conformation of the nucleotide. The C site is more spacious, and the crystal structures show that AMP binds in the anti conformation and GMP in the syn. The Ser[47] hydrogen bond with the GMP 2-amino group provides a modest 3-fold-increased binding affinity for GMP to the C site relative to those of IMP and AMP, which lack the 2-amino group (Table 2).

There is a second specificity determinant. Nucleoside mono- and diphosphates have equal access to the A site, whereas nucleoside monophosphates are favored in the C site. This is because there are no barriers to monophosphates or diphosphates in the A site, whereas there is a steric clash half-saturation that is similar to that for AMP (Table 2). Thus, rearrangements of the PRPP loop can accommodate a nucleoside diphosphate in the C site.

Finally, a $Mg^{2+}$ is required for nucleotide binding to both the C and A sites. Furthermore, it has been reported that distinct metal ions are required for both inhibition and enzymatic catalysis. The $Mg^{2+}$ allows the C site nucleotide to bind to the protein via its coordination to the ribose 2'-OH and 3'-OH and the Asp[347] and Asp[346] carboxylates and helps to neutralize the relatively high local negative charge in the vicinity of these aspartate residues. The importance of this metal ion for inhibition is emphasized by the observation that binding of nucleotide to either site is abolished in the absence of $Mg^{2+}$, as determined by equilibrium dialysis.

Synergistic Nucleotide Binding.

Synergistic binding of the ADP-GMP pair accounts for the observed synergistic inhibition. In the presence of GMP the $K_d$ for ADP was decreased 20-fold from approximately 214 to 11 μM. It is necessary, however, to recognize that binding of ADP to the free enzyme is complex, involving cooperative binding to two A sites and two C sites per dimer. Thus, the $K_d$ of 214 μM, in this instance, is an operational assessment of half-saturation of the two sites. In the presence of GMP, the $K_d$ for ADP is more simply defined as half-saturation of the A site. In the reciprocal experiment, the $K_d$ for GMP was decreased from an unmeasurable concentration to 25 μM in the presence of ADP. Assuming a synergism of 20-fold, we estimate a $K_d$ of GMP for the free enzyme of approximately 500 μM.

The structural model for the enzyme-ADP-GMP complex explains the physical basis for synergism. There are three key points. First, ADP and GMP are each bound to their preferred sites. For this nucleotide pair, there is minimal competition between nucleotides for each site. Competition between nucleotides for a site minimizes the opportunity for a productive nucleotide—nucleotide interaction. Even though AMP and IMP have similar affinities for binding to the C site (Table 2), competition of AMP, but not IMP, with ADP for the A site explains the difference in synergism between IMP-ADP and AMP-ADP (Table 3). Second, the nucleotide—nucleotide interaction is not possible with nucleoside monophosphates in both sites. Third, the octahedrally coordinated $Mg^{2+}$ is important not only for inhibition by nucleotides but also for synergism. This requirement is explained by the structural model in which the ribose 2'- and 3'-hydroxyls of the C site nucleotide are ligands to the $Mg^{2+}$.

Synergistic Inhibition.

There are two key features relating to the synergistic inhibition of glutamine PRPP amidotransferase by adenine and guanine nucleotide pairs. First, the inhibition by each nucleotide is amplified. AMP is the most potent single nucleotide inhibitor. However, as a consequence of synergism, an ADP/GMP mixture inhibits more strongly than AMP. Second, inhibition by one nucleotide is dependent upon the fixed concentration of the partner. As shown in Table 3, values for 50% inhibition by ADP were dependent upon the fixed GMP concentration. This is because of competition between GMP and PRPP for the C site. In the absence of PRPP, the C site was saturated by 0.25 mM GMP with ADP bound to the A site (Table 2). However, 10-fold or higher concentrations of GMP were required for C site saturation when PRPP was present (Table 3).

It is obviously technically impossible to determine the concentration required for 50% inhibition by one nucleotide in the presence of a saturating concentration of a second. For this reason, synergism was defined as the increased inhibition by one nucleotide at an arbitrarily fixed concentration of the partner. The ADP-GMP synergism varies in parallel with the concentration of either nucleotide, thus further amplifying the regulatory response. The synergism for ADP-IMP was about half that of ADP-GMP, and there was little or no synergism for ADP-AMP and GMP-AMP. Two other nucleotide pairs, ADP-GDP and GDP-GMP, have also been reported to give synergistic inhibition.

Competition between PRPP and Nucleotide for the C Site.

There are two important consequences of C site competition between PRPP and nucleotide. First, in the presence of substrate (PRPP), binding of ADP at the A site (and subsequent enzyme inhibition) is impacted by the competition between PRPP and the nucleotide for the C site. This amplifies synergism, as shown by comparing the 20-fold synergistic binding of ADP (+GMP) (Table 3), determined in the presence of PRPP. Second, competition between nucleotide and PRPP can explain the more effective inhibition by AMP compared with that by ADP. Given the fact that the apparent $K_d$ values for ADP and AMP are identical (Table 2), it is surprising that 5-fold higher concentrations of ADP, relative to those of AMP, were required for 50% inhibition (Table 3). A plausible explanation is that PRPP competes more effectively with ADP for the C site due to steric clash of the ADP β-phosphate with residues of the PRPP loop. Furthermore, binding of PRPP to the C site may exclude binding of ADP but not AMP to the A site due to overlap of the binding sites for the β-phosphate of PRPP and the β-phosphate of ADP in the A site.

EXAMPLE 2

Mutational Analysis of the A Site and B Site

Site directed mutagenesis was utilized to modify amino acids comprising the A site and C site domains of the glutamine PRPP amidotransferase. These modified forms of amidotransferase were analyzed to determine the impact of the mutations on end-product inhibition and enzymatic activity. Inhibition by nucleotides was determined as described in Example 1.

Mutations of A and C Site Residues That Interact with Nucleotides.

Four residues that interact with nucleotides bound in the A and C sites and have been replaced and the effects of these mutations on inhibition and synergism was investigated. Summarized data are given in Table 3 for inhibition of mutant enzymes S283A, K305Q, R307Q, and S347A by individual nucleotides and nucleotides mixtures.

The $Ser^{283}$ hydroxyl is a ligand to the octahedrally coordinated $Mg^{2+}$ in the C site. The other five ligands are the carboxylates of $Asp^{345}$ and $Asp^{346}$, the ribose 2'- and 3'-hydroxyls of the C site nucleotide, and a water molecule. Furthermore, the $Pro^{281}$-cis-$Asp^{282}$-$Ser^{283}$ turn occupies a central location between the A and C sites, and mutations here might be expected to impact nucleotide binding in either site. $I_{0.5}$ concentration for AMP and ADP were increased 5–7 fold in the S283A mutant relative to that of the wild type enzyme, whereas the inhibition by GMP was similar for the mutant and wild type.

These results suggest that S283A has a greater impact on nucleotide binding to the A site than to the C site because AMP and ADP bind to both nucleotide sites, whereas high-affinity GMP binding is predominantly to the C site. Inhibition by an ADP-GMP mixture demonstrated substantially reduced synergistic inhibition by S283A. With an ADP-GMP mixture, a 30-fold higher concentration of ADP and a 13-fold higher concentration of GMP were required for 50% inhibition compared to that of wild type. Synergism for the ADP-GMP pair was 4.5-fold, the average calculated from $I_{0.5}$ concentrations for ADP (synergism of 5.0) and GMP (synergism of 3.9), compared to 61-fold for wild type. Loss of synergism thus could account for the defective inhibition by the ADP-GMP mixture even though the inhibition by GMP alone was not perturbed.

The impact of S283A on the A site is explained most directly by effects on the $Pro^{281}$-cis-$Asp^{282}$-$Ser^{283}$ turn, which binds the phosphate moiety of the A site nucleotide. The Ser283 hydroxyl Mg2+ ligand, lost in the mutation, is likely replaced by water and is expected to cause subtle changes in the conformation of the $Pro^{281}$-cis-$Asp^{282}$-$Ser^{283}$ turn. Such changes could perturb A site nucleotide binding directly or indirectly through salt bridges between the A site nucleotide α-phosphate and the side chain of $Lys^{305}$ and $Arg^{307}$.

Thus the large reduction in synergism in the S283A mutant provides evidence that the $Ser^{283}$ β-hydroxyl ligand to the $Mg^{2+}$ is required for synergism. This interaction positions the unusual $Pro^{281}$-cis-$Asp^{282}$-$Ser^{283}$ turn, which is part of both the A and C sites. In the absence of $Mg^{2+}$ coordination in the S283A mutant, the $Pro^{281}$-cis-$Asp^{282}$-$Ser^{283}$ turn may have a different conformation, repositioning the A and C sites with respect to one another. A very small structural change could effectively eliminate the interaction between the C site ribose 2'-OH and the A site ADP β-phosphate, and thus decrease synergism. Without this nucleotide—nucleotide interaction, there is minimal synergistic binding for AMP-GMP.

$Lys^{305}$ and $Arg^{307}$ interact with nucleotide in the A site. In addition to the salt bridges just described, the backbone oxygen of $Lys^{305}$ forms a base-specific hydrogen bond with adenine $N_6$. $Arg^{307}$ $N_\eta$ interacts with the β-phosphate and also with the carboxylate of cis-$Asp^{282}$. The latter interaction links $Arg^{307}$ with $Ser^{283}$. The two A site mutations, K305Q and R307Q, had similar effects. $I_{0.5}$ concentrations for inhibition by a single nucleotide were increased 3 to 6-fold compared to that of the wild type. This effect was amplified for inhibition by the ADP-GMP nucleotide pair, for which $I_{0.5}$ values were increased 15 to 75-fold. Synergism for the ADP-GMP pair was approximately 111 for R307Q (average of 156 and 66) and 68 (average of 97 and 38) for Lys 305Q, variations of less than 2-fold from the value of the wild type. Although these residues interact with the A-site nucleotide, the perturbations were comparable for inhibition by ADP at the A site and by GMP at the C site. As a consequence of synergism, decreased affinity of ADP for the mutant A site perturbs inhibition by GMP at the C site.

The side chain of $Ser^{347}$ makes a key, base-specific interaction with the guanine 2-amino group of GMP in the C site. This H bond stabilizes the syn conformation of GMP in the C site and is expected to contribute to the C site preference for GMP. IMP lacks the 2-amino substituent but is otherwise identical to GMP. For the wild type enzyme, $I_{0.5}$ was 6-fold higher for IMP than for GMP, determined in each case with ADP bound to the A site, and synergism was 2-fold lower, thus supporting the contribution of $Ser^{347}$ to GMP binding in the C site. In the S347A mutant, there were comparable changes for inhibition by GMP and IMP at the C site. $I_{0.5}$ GMP and $I_{0.5}$ IMP increased 3-fold and 2-fold, respectively, compared to that of the wild type. Synergism was similar for GMP-ADP in S347A, for IMP-ADP in S347A, and for IMP-ADP in the wild type, with values of 26–33 which were about half of that obtained with GMP-ADP in the wild type enzyme. Thus, GMP and IMP exhibit similar synergism with ADP in the absence of the guanine-specific hydrogen bond to $Ser^{347}$. The S347A mutation does not, however, equalize the inhibition for GMP and IMP; GMP is still a better inhibitor. In the absence of the hydrogen bond to $Ser^{347}$, GMP may bind in the anti conformation, which might afford other hydrogen bonding opportunities for the 2-amino group. Interpretation of the S347A data is also complicated by a second hydrogen bond from the side chain of $Ser^{347}$ to that of $Asp^{346}$. Subtle structural changes in the PRPP binding loop may result from elimination of this hydrogen bond in S347A. This is supported by measurements of $K_{m\ PRPP}$. Values of $K_{m\ PRPP}$ of 75–81 $\mu$M were obtained for the wild type, S283A, K305Q, and R307Q enzymes, but a $K_{m\ PRPP}$ of 182 $\mu$M was obtained for the S347A enzyme (data not shown).

Inhibition Requires Nucleotide Binding to both A and C Sites.

Two lines of evidence support the conclusion that binding of nucleotides to both sites is necessary for inhibition. First, by direct measurement the affinity of the C site for GMP was determined to be 3-fold higher than that, for AMP, in each case with ADP bound to the A site. The fact that half-saturation of the A plus C sites required 240 $\mu$M AMP whereas GMP binding was too weak to detect indicates that weak affinity of GMP for the A site precluded detection of C site binding. Second, A site mutations K305Q and R307Q had as much of an effect on inhibition by GMP as on inhibition by ADP, and a C site mutation, S347A, likewise had a comparable effect on inhibition by these two nucleotides. If nucleotide binding to one site were sufficient for inhibition, A site mutations should preferentially disable ADP binding and inhibition, and the C site mutation should preferentially perturb GMP binding and inhibition. The S283A mutant is closest to having selective loss of inhibition by one nucleotide. In this mutant, inhibition by GMP was similar to that of the wild type whereas there was 5–7-fold-decreased inhibition by AMP or by ADP. However, even in this mutant, synergistic inhibition at both the A and C sites was decreased for the ADP-GMP pair. In contrast to the *E. coli* enzyme where an A site mutation selectively decreased binding to the A site and the inhibition (8), mutations in either of the nucleotide sites of the B. Subtilis glutamine PRPP amidotransferase perturbed the function at both sites.

Discussion

Of the mutations that perturbed nucleotide binding, synergism was affected most by the $Ser^3$ replacement and little, if at all, by replacements of $Lys^{305}$ and $Arg^{307}$. ADP/GMP synergism was reduced only minimally from 60-fold in the wild type to 35-fold in the S347A mutant. Two results stand out. In assays of A and C site function using ADP-GMP pair, inhibition at both sites was comparably perturbed in each of the mutants. That is, in no case did a mutation selectively disable one site. Second, the inhibition at the A and C sites by the nucleotide mixture was decreased more than inhibition by individual nucleotides. Thus, site—site interaction was more sensitive to mutational disruption than an individual site. In this context, the $Pro^{281}$-cis-$Asp^{282}$-$Ser^{283}$ turn could be called the "synergistic turn", emphasizing its key role in synergism.

The above mutational analysis was conducted on *Bacillus subtilis* glutamine PRPP amidotransferase. However, the amino acid sequence of the functional sites, and thus the structure of these sites, of glutamine PRPP amidotransferases of different organisms is highly conserved. Therefore mutations similar to those described above are expected to have the same effect for homologous enzymes isolated from different organisms, such as *E. coli* and other prokaryotic organisms used for commercial production of nucleosides or nucleotides.

What is claimed is:

1. A modified *E. coli* glutamine PRPP amidotransferase wherein the amino acid sequence of said modified *E. coli* amidotransferase differs from the amino acid sequence of a native *E. coli* glutamine PRPP amidotransferase in that one or more amino acid residues of said modified amidotransferase are substituted at positions equivalent to amino acid positions in Bacillus amidotransferase selected from the group consisting of 282, 283, 307, and 347 of SEQ ID NO: 1 with amino acids not native to said position or positions in *E. coli* wherein said equivalent positions are identified based on comparison of amino acid sequences of Bacillus and *E. coli* glutamine PRPP amidotransferases and wherein said modified *E. coli* amidotransferase is less sensitive to end-product inhibition than is the native *E. coli* glutamine PRPP amidotransferase.

2. The modified glutamine PRPP amidotransferase of claim 1 wherein the amino acid substitution reduces synergistic binding of adenine and guanine nucleotides to the amidotransferase.

* * * * *

UNITED STATES PATENT AND TRADEMARK OFFICE
CERTIFICATE OF CORRECTION

PATENT NO. : 6,586,216 B2
DATED : July 1, 2003
INVENTOR(S) : Zalkin et al.

It is certified that error appears in the above-identified patent and that said Letters Patent is hereby corrected as shown below:

Column 1,
Lines 11-13, please enter the following paragraph:
-- GOVERNMENT RIGHTS
   Research relating to this invention was supported in part by the U.S. government undert Grant Nos. GM24658, DK42303, and GM47112 awarded from the National Institutes of Health. The U.S. Government may have certain right in this invention. --

Signed and Sealed this

Tenth Day of August, 2004

JON W. DUDAS
*Acting Director of the United States Patent and Trademark Office*

SEQUENCE LISTING

<160> NUMBER OF SEQ ID NOS: 1

<210> SEQ ID NO 1
<211> LENGTH: 465
<212> TYPE: PRT
<213> ORGANISM: Bacillus subtilis

<400> SEQUENCE: 1

Cys Gly Val Phe Gly Ile Trp Gly His Glu Glu Ala Pro Gln Ile Thr
1               5                   10                  15

Tyr Tyr Gly Leu His Ser Leu Gln His Arg Gly Gln Glu Gly Ala Gly

-continued

```
                20                  25                  30
Ile Val Ala Thr Asp Gly Glu Lys Leu Thr Ala His Lys Gly Gln Gly
                35                  40                  45

Leu Ile Thr Glu Val Phe Gln Asn Gly Glu Leu Ser Lys Val Lys Gly
 50                  55                  60

Lys Gly Ala Ile Gly His Val Arg Tyr Ala Thr Ala Gly Gly Gly Gly
 65                  70                  75                  80

Tyr Glu Asn Val Gln Pro Leu Leu Phe Arg Ser Gln Asn Asn Gly Ser
                 85                  90                  95

Leu Ala Leu Ala His Asn Gly Asn Leu Val Asn Ala Thr Gln Leu Lys
                100                 105                 110

Gln Gln Leu Glu Asn Gln Gly Ser Ile Phe Gln Thr Ser Ser Asp Thr
                115                 120                 125

Glu Val Leu Ala His Leu Ile Lys Arg Ser Gly His Phe Thr Leu Lys
    130                 135                 140

Asp Gln Ile Lys Asn Ser Leu Ser Met Leu Lys Gly Ala Tyr Ala Phe
145                 150                 155                 160

Leu Ile Met Thr Glu Thr Glu Met Ile Val Ala Leu Asp Pro Asn Gly
                165                 170                 175

Leu Arg Pro Leu Ser Ile Gly Met Met Gly Asp Ala Tyr Val Val Ala
                180                 185                 190

Ser Glu Thr Cys Ala Phe Asp Val Val Gly Ala Thr Tyr Leu Arg Glu
                195                 200                 205

Val Glu Pro Gly Glu Met Leu Ile Ile Asn Asp Glu Gly Met Lys Ser
    210                 215                 220

Glu Arg Phe Ser Met Asn Ile Asn Arg Ser Ile Cys Ser Met Glu Tyr
225                 230                 235                 240

Ile Tyr Phe Ser Arg Pro Asp Ser Asn Ile Asp Gly Ile Asn Val His
                245                 250                 255

Ser Ala Arg Lys Asn Leu Gly Lys Met Leu Ala Gln Glu Ser Ala Val
                260                 265                 270

Glu Ala Asp Val Val Thr Gly Val Pro Asp Ser Ser Ile Ser Ala Ala
            275                 280                 285

Ile Gly Tyr Ala Glu Ala Thr Gly Ile Pro Tyr Glu Leu Gly Leu Ile
    290                 295                 300

Lys Asn Arg Tyr Val Gly Arg Thr Phe Ile Gln Pro Ser Gln Ala Leu
305                 310                 315                 320

Arg Glu Gln Gly Val Arg Met Lys Leu Ser Ala Val Arg Gly Val Val
                325                 330                 335

Glu Gly Lys Arg Val Val Met Val Asp Asp Ser Ile Val Arg Gly Thr
                340                 345                 350

Thr Ser Arg Arg Ile Val Thr Met Leu Arg Glu Ala Gly Ala Thr Glu
                355                 360                 365

Val His Val Lys Ile Ser Ser Pro Pro Ile Ala His Pro Cys Phe Tyr
    370                 375                 380

Gly Ile Asp Thr Ser Thr His Glu Glu Leu Ile Ala Ser Ser His Ser
385                 390                 395                 400

Val Gly Glu Ile Arg Gln Glu Ile Gly Ala Asp Thr Leu Ser Phe Leu
                405                 410                 415

Ser Val Glu Gly Leu Leu Lys Gly Ile Gly Arg Lys Tyr Asp Asp Ser
                420                 425                 430

Asn Cys Gly Gln Cys Leu Ala Cys Phe Thr Gly Lys Tyr Pro Thr Glu
                435                 440                 445
```

```
Ile Tyr Gln Asp Thr Val Leu Pro His Val Lys Glu Ala Val Leu Thr
    450                 455                 460
Lys
465
```